United States Patent [19]

Saito et al.

[11] Patent Number: 4,818,430
[45] Date of Patent: Apr. 4, 1989

[54] 3,6-DIPHENYLPYRIDAZINES

[75] Inventors: Shinichi Saito; Takashi Inukai; Hiromichi Inoue; Kazutoshi Miyazawa; Kouji Ohno, all of Yokohamashi, Japan

[73] Assignee: Chisso Corporation, Tokyo, Japan

[21] Appl. No.: 98,932

[22] Filed: Sep. 15, 1987

[30] Foreign Application Priority Data

Sep. 16, 1986 [JP] Japan .................. 61-217388

[51] Int. Cl.$^4$ .................. C09K 19/52; C09K 19/34; C07D 237/00; C07D 237/02
[52] U.S. Cl. .................. 252/299.61; 252/299.01; 252/299.5; 350/350 R; 350/350 S; 544/224
[58] Field of Search .......... 252/299.61, 299.5, 299.01; 350/350 R, 350 S; 544/224

[56] References Cited

U.S. PATENT DOCUMENTS

| | | | |
|---|---|---|---|
| 4,452,718 | 6/1984 | Schadt et al. | 252/299.61 |
| 4,565,425 | 1/1986 | Petrzilka et al. | 252/299.61 |
| 4,595,521 | 6/1986 | Petrzilka et al. | 252/299.61 |
| 4,657,695 | 4/1987 | Saito et al. | 252/299.61 |
| 4,676,604 | 6/1987 | Petrzilka | 252/299.61 |
| 4,713,197 | 12/1987 | Eidenschink et al. | 252/299.61 |
| 4,723,005 | 2/1985 | Huynh-Ba et al. | 252/299.61 |

FOREIGN PATENT DOCUMENTS

| | | | |
|---|---|---|---|
| 174541 | 3/1986 | European Pat. Off. | 252/299.61 |
| 3515373 | 11/1986 | Fed. Rep. of Germany | 252/299.61 |
| 86/06401 | 11/1986 | World Int. Prop. O. | 252/299.61 |

OTHER PUBLICATIONS

Schubert, H, Wiss. Z. Univ. Halle XIX'70M, H.5, 5.1–18.
Demus, D., et al., Flussige Kristalle in Tabellen, VEB Deutscher Verlag fur Grundstoffindustrie, Leipzig, pp. 259–260 (1970).
Demus D., et al., Flussige Kristalle in Tabellen II, VEB Deutscher Verlag fur Grundstoffindustrie, Leipzig, pp. 344–400 (1984).
Gray, G. W., et al., Liquid Crystals & Plastic Crystals, vol. 1, John Wiley & Sons, Ltd., N.Y., pp. 142–143 (1974).
C.A. 102:78810h (1985).
C.A. 106:166738d (5/18/87).
C.A. 104:216956e (6/16/86).
C.A. 104:139769s (4/21/86).

*Primary Examiner*—Teddy S. Gron
*Attorney, Agent, or Firm*—Wenderoth, Lind & Ponack

[57] ABSTRACT

A compound useful as a constituent of liquid crystal materials for ferroelectric liquid crystal display elements and a liquid crystal composition containing the same are provided, which compound is expressed by the formula

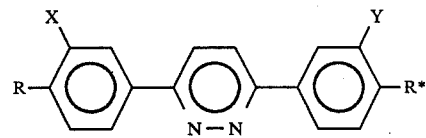

wherein R represents a linear or branched chain alkyl group or alkoxy group each of 1 to 20 carbon atoms, R* represents an optically active group of 3 to 16 carbon atoms and X and Y each represent H or F.

3 Claims, No Drawings

3,6-DIPHENYLPYRIDAZINES

BACKGROUND OF THE INVENTION

1. Field of the Invention

This invention relates to a novel liquid crystal compound and more particularly it relates to a liquid crystal compound having an optically active group and a chiral smectic liquid crystal composition containing the same.

2. Description of the Related Art

At present, a TN (twisted Nematic) type display mode has been most broadly employed for liquid crystal display elements. This TN liquid crystal display has a number of advantages such as low driving voltage, small power consumption, etc. However, such display elements are inferior in the aspect of the response rate to emissive type display elements such as cathode ray tube, electroluminescence, plasma display, etc. A novel TN type display element having the twist angle changed to a range of 180° to 270° has also been developed, but such a display element is still inferior in the aspect of the response rate. As described above, various efforts for improvement therein have been made, but any of these have not yet succeeded. However, in the case of a novel display mode using ferroelectric liquid crystals, there is a possibility of notable improvement in the response rate (Clark et al, Applied Phys. lett., 36, 899 (1980)). This mode makes use of chiral smectic phases such as chiral smectic C phase (hereinafter abbreviated to SC* phase). The phases exhibiting ferroelectric properties are not only SC* phase alone, but also it has been known that chiral smectic phases F, G, H, I, etc. also exhibit ferroelectric properties. In order to make use of such a ferroelectric liquid crystal for display elements, it has been not only required that such ferroelectric liquid crystal phases be exhibited over a broad temperature range including room temperature, but also various characteristics have been required for such elements.

SUMMARY OF THE INVENTION

The object of the present invention is to provide a compound useful as a constituent of liquid crystal materials for such a ferroelectric liquid crystal display element.

The present invention resides in a compound expressed by the formula

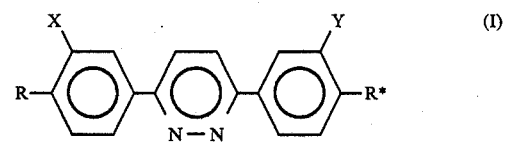

wherein R represents a linear or branched chain alkyl group or alkoxy group each of 1 to 20 carbon atoms, R* represents an optically active group of 3 to 16 carbon atoms and X and Y each represent H or F,
a liquid crystal composition containing the same and
a liquid crystal display element using this composition.

DETAILED DESCRIPTION OF PREFERRED EMBODIMENTS

Concrete examples of R* as the optically active group of the formula (I) are 2-methylbutyl, 2-methylbutoxy, 2-methylbutanoyloxy, 3-methylpentyl, 3-methylpentoxy, 3-methylpentanoyloxy, 4-methylhexyloxy, 5-methylheptyloxy, 6-methyloctyloxy, 1-methylheptyloxy, 1-methylbutoxy, 1-methylheptanoyloxy, 1-methylbutanoyloxy, 2-fluoropropoxy, 2-fluoropropoxy, 2-chloropropanoyloxy, 2-fluorooctyloxy, 2-chlorooctyloxy, 2-cyano-propoxy, 2-cyano-hexyloxy, 2-(2'-methylbutoxy)-ethoxy, 2-(3'-methylpentoxy)-ethoxy, 2-(4'-methylhexyloxy)-ethoxy, 3-(2'-methylbutoxy)-propoxy, 4-(2'-methylbutoxy)-butoxy, 2-ethoxy-1-propoxy, 2-butoxy-1-propoxy, 2-pentoxy-1-propoxy, 3-propoxy-1-butoxy, 3-hexyloxy-1-butoxy, 2-ethoxy-propanoyloxy, 2-propoxy-propanoyloxy, 2-butoxypropanoyloxy, 2-methyl-3-ethoxy-1-propoxy, 2-methyl-3-butoxy-1-propoxy, 2-butanoyloxy-1-propoxy, 2-pentanoyloxy-1-propoxy, 2-(2'-butoxypropanoyloxy)-1-propoxy, 2-(2'-chloro-3'-methylpentanoyloxy)-1-propoxy, 2-(2'-chloropropanoyloxy)-1-propoxy, etc.

The values of the physical properties of the representative compounds of the formula (I) are shown in Table 1.

TABLE 1

| Compound No. | R | X | Y | R* | Absolute configuration | C | SX | SC* | SA | Ch | I | Example No. |
|---|---|---|---|---|---|---|---|---|---|---|---|---|
| 1 | C9H19 | H | H | —O—CH(*)—C6H13, CH3 | S | • 126 | — | • 154 | — | — | • | 1 |
| 2 | C9H19 | H | F | —O—CH(*)—C6H13, CH3 | S | • 105 | — | • 137 | — | — | • | 2 |
| 3 | C3H7 | H | H | —OC(=O)—(CH2)3CH(*)CH2CH3, CH3 | S | • 193.8 | — | • 227.6 | — | • 232.0 | • | 3 |
| 4 | C3H7 | H | H | —OC(=O)—CH(*)—O—(CH2)3CH3, CH3 | S | • 170.8 | — | • 177.3 | • 208.3 | — | • | |

(Physical properties of 3,6-diphenylpyridazines; Phase transition point (°C.))

TABLE 1-continued

Physical properties of 3,6-diphenylpyridazines

| Compound No. | In formula (I) R | X | Y | R* | Absolute configuration | Phase transition point (°C.) C | SX | SC* | SA | Ch | I | Example No. |
|---|---|---|---|---|---|---|---|---|---|---|---|---|
| 5 | C$_3$H$_7$ | H | H | $-O-CH_2\overset{*}{C}H(CH_3)CH_2CH_3$ | S | • 183.2 | — | • 204.4 | — | • 214.1 | • | |
| 6 | C$_3$H$_7$ | H | H | $-O-\overset{*}{C}H(CH_3)-C_6H_{13}$ | S | • 116.0 | — | • 133.6 | — | • 137.8 | • | |
| 7 | C$_3$H$_7$ | H | H | $-O-(CH_2)_4-\overset{*}{C}H(CH_3)CH_2CH_3$ | S | • 143.0 | — | • 219.5 | — | • 222.7 | • | |
| 8 | C$_3$H$_7$ | H | H | $-O-(CH_2)_5-\overset{*}{C}H(CH_3)-CH_2CH_3$ | S | • 146.0 (• 135.9) | | • 228.0 | — | — | • | |
| 9 | C$_3$H$_7$ | H | H | $-O-(CH_2)_7-\overset{*}{C}H(CH_3)CH_2CH_3$ | S | • 128.8 | • 140 | • 227.9 | — | — | • | |
| 10 | C$_3$H$_7$ | H | H | $-OCH_2\overset{*}{C}H(CH_3)OC(O)-(CH_2)_2CH_3$ | S | • 165.0 | — | • 172.9 | — | — | • | |
| 11 | C$_3$H$_7$ | H | H | $-OCH_2\overset{*}{C}H(CH_3)OC(O)-(CH_2)_3CH_3$ | S | • 165.8 | — | • 166.7 | — | — | • | |
| 12 | C$_3$H$_7$ | H | H | $-OCH_2\overset{*}{C}H(CH_3)OC(O)-\overset{*}{C}H(CH_3)CH_2CH_3$ | S.S | • 183.5 | — | — | (• 160.5) | (• 162.0) | • | |
| 13 | C$_3$H$_7$ | H | H | $-S-CH_2\overset{*}{C}H(CH_3)OC(O)(CH_2)_3\overset{*}{C}H(CH_3)CH_2CH_3$ | S.S | • 148.0 | — | • 152.3 | — | — | • | |
| 14 | C$_3$H$_7$ | H | H | $-OCH_2\overset{*}{C}H(CH_3)-OC(O)-\overset{*}{C}H(CH_3)O(CH_2)_2CH_3$ | S.S | • 163.0 | — | (• 150.0) | — | (• 155.8) | • | |

Most of the compounds of the formula (I) of the present invention exhibit SC* phase within a broad high temperature range. Further, among the compounds of the formula (I), those which exhibit smectic phases other than SC* phase are few. Thus, it can be said that the compounds of the formula (I) are very effective as a component for exhibiting SC* phase within a high temperature range and also as a component for inhibiting exhibition of smectic phases other than SC* phase, among components of compositions exhibiting ferroelectric liquid crystal phases.

Namely, when one or several kinds of the compounds of the present invention are mixed in suitable quantities with a liquid crystal material exhibiting SC* phase or achiral smectic C phase at medium and low temperatures, it is possible to obtain a liquid crystal material exhibiting ferroelectric liquid crystal phases within a broad temperature range including low temperatures and room temperature. Further, some of the compounds of the present invention have a large spontaneous polarization value Ps; hence they are effective for preparing display elements having a high response rate.

When a chiral smectic liquid crystal composition is constituted, it is possible to constitute it using a plurality of the compounds of the formula (I), alone, and it is also possible to prepare a liquid crystal composition exhibiting SC* phase by mixing the compound of the formula (I) with another chiral or achiral smectic liquid crystal. In addition, the racemate corresponding to the compound of the formula (I) may be similarly prepared by using a raw material for the racemate in place of an optically active substance in the preparation of an optically active substance (I) as described later, and the resulting racemate has almost the same phase transition points as those of the compound of the formula (I). However, the racemate exhibits SC phase in place of SC* phase, and when it is added to the optically active substance (I), it is possible to use it for adjusting the pitch of the chiral smectic phase thereof. Further, the compound of the formula (I) has an optically active carbon atom; hence when the compound is added to a nematic liquid crystal, it has a capability of inducing a twist structure. A nematic liquid crystal having a twist structure i.e. a chiral nematic liquid crystal does not form the so-called reverse domain of TN type display elements; hence it is usable as an agent for preventing the reverse domain from forming.

Further, some of chiral nematic liquid crystal compositions prepared by adding the compound of the present invention to a nematic liquid crystal composition have a negative temperature dependency in the chiral pitch thereof, as described in Example 5. As to the chiral pitch of most of chiral dopants to be added to nematic liquid crystals currently used, the pitch becomes longer with temperature rise, but it has also been reported that in the case of some of chiral dopants, the chiral pitch becomes shorter with temperature rise, and further it has been known that these substances reduce the temperature range in the threshold voltage as an electrooptical characteristic of TN type display elements (the 33rd Associated Lecture Meeting related to Applied physics, 1986, Spring), Collected Preliminary Manuscripts for Lecture 1 p-G-7 (p. 78) and JAPAN DISPLAY '86, Collected Preliminary Manuscripts for Lecture, 8.3 (p. 286–289)).

Since the compound of the present invention has similar physical properties to those of the above compounds, it is possible to reduce the temperature dependency of the threshold voltage of chiral nematic liquid crystal compositions having the compound added thereto.

Further, apart from this, in the case of the socalled super TN type display having the twist angle in TN type display increased up to a range of 180° to 270°, the temperature dependency of pitch notably reduces the display quality; thus when a chiral nematic liquid crystal composition having the compound of the present invention added thereto is used, it is possible to prepare a superior super TN type display element whose display quality is not damaged by the temperature change.

As described above, the compound of the present invention is also useful as a chiral component compound of chiral nematic compositions.

Next, the preparation of the compound of the present invention will be described. The compound of the formula (I) may be prepared for example according to the following scheme:

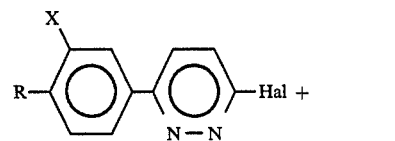

(IIa)

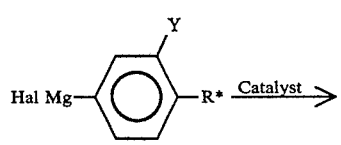

(IIIa)

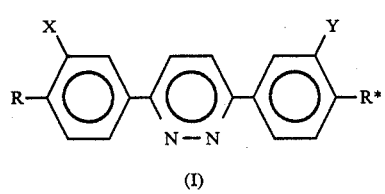

(I)

or

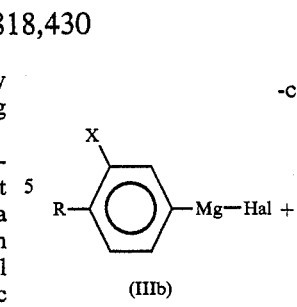

(IIIb)

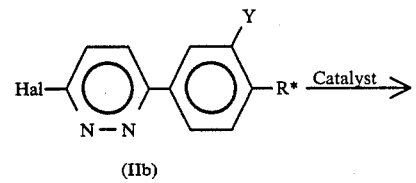

(IIb)

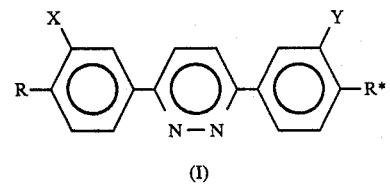

(I)

Preparation of a compound of the above formula (IIa) wherein X represents hydrogen atom is disclosed in a literature (Z. Chem., 17 [9] 333 (1977)). A compound of the above formula (IIb) wherein Y represents hydrogen atom and a compound of the formula (IIa) wherein X represents fluorine atom are also similarly obtained according to a method described in the literature.

As the catalyst, it is preferred to use $NiL_2Cl_2$ wherein L represents a phosphine ligand, and as the $L_2$ is particularly preferred to be $(PPh_3)_2$, $Ph_2P-(CH_2)_3-PPh_2$, $Ph_2P-(CH_2)_2-PPh_2$, etc.

The liquid crystalline compound and the composition of the present invention will be described in more detail by way of Examples.

EXAMPLE 1

Preparation of S-3-(4'-nonylphenyl)-6-(4'-1-methylheptyloxy)phenyl)-pyridazine (a compound of the formula (I) wherein R represents nonyl, R* represents 1-methylheptyloxy and X and Y each represent hydrogen atom)

3-Chloro-6-(4'-nonylphenyl)-pyridazine (phase transition points: 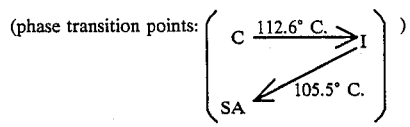 )

(8 g) prepared according to the method described in the above literature was dissolved in tetrahydrofuran (100 ml), followed by cooling the solution in an ice bath, adding Ni(dppp)Cl$_2$ (dichloro-1,3-bis(diphenylphosphino)propanenickel) (0.1 g), agitating the mixture for 15 minutes, dropwise adding thereto a Grignard reagent obtained by reacting magnesium with an optically active p-1-methylheptyloxybromobenzene (10 g) prepared by reacting p-bromophenol with R(-)-octyl-p-toluenesulfonate, in tetrahydrofuran, agitating the mixture in an ice bath for 2 hours, successively further agitating it at room temperature for 2 hours, allowing it to stand overnight, adding toluene (200 ml), further adding 6N-hydrochloric acid, separating the resulting organic layer, washing it with water, then with an alkali and further with water till the washing water became neutral, drying it with MgSO4, distilling off toluene, purifying the residue according to column chromatography using activated alumina (30 g) and toluene as an eluent, and twice recrystallizing from ethyl acetate (200 ml) to obtain the captioned 3-(4'-nonylphenyl)-6-(4'-(1-methylheptyloxy)phenyl)-pyridazine (5.0 g). This product had a m.p. of 126° C., exhibited SC* phase and formed an isotropic liquid at 154° C. It was analyzed according to high rate liquid chromatography to give a purity of 99.6%. Its proton NMR was as follows (in CDCl3 and based on TMS):

| δ (ppm) | | | |
|---|---|---|---|
| 8.07 | d | 2H | J = 8 Hz |
| 8.05 | d | 2H | J = 8 Hz |
| 7.78 | s | 2H | |
| 7.30 | d | 2H | J = 8 Hz |
| 7.00 | d | 2H | J = 8 Hz |
| 4.67~4.17 | m | 1H | |
| 2.67 | t | 2H | J = 7 Hz |
| 2.02~0.67 | m | 32H | |

EXAMPLE 2

Preparation of
S-3-(4'-nonylphenyl)-6-(3'-fluoro-4'-(1-methylheptyloxy)phenyl)-pyridazine (a compound of the formula (I) wherein R represents nonyl, R* represents 1-methylheptyloxy, X represents hydrogen atom and Y represents fluorine atom)

3-Chloro-6-(4'-nonylphenyl)-pyridazine (2 g), 3-fluoro-4-(1-methylheptyloxy)phenylmagnesium bromide obtained by reacting magnesium with 1-(1-methylheptyloxy)-2-fluoro-4-bromobenzene (5.0 g) and Ni(dppp)Cl2 (0.1 g) as a catalyst were reacted in tetrahydrofuran in the same manner as in Example 1, followed by carrying out post-treatment and purification in the same manner as in Example 1, to obtain the captioned S-3-(4'-nonylphenyl)-6-(3'-fluoro-4'-(1-methylheptyloxy)phenyl)-pyridazine (1.0 g). This product had a m.p. of 105° C., exhibited SC* phase at temperatures higher than that and formed an isotropic liquid at 136.5°-137.0° C. It was analyzed according to high rate liquid chromatography to give a purity of 99.8%.

EXAMPLE 3

Preparation of
S-3-(4'-(5''-methylheptanoyloxy)phenyl)-6-(4'-propylphenyl)-pyridazine (a compound of the formula (I) wherein R represents propyl, R* represents 5-methylheptanoyloxy and X and Y both represent hydrogen atom)

(a) Preparation of
3-(4'-methoxyphenyl)-6-(4'-propylphenyl)-pyridazine

3-Chloro-6-(4'-propylphenyl)-pyridazine prepared according to a method disclosed in a known literature (m.p.: 127.6°-129.6° C.) (60.0 g) was dissolved in tetrahydrofuran (THF) (700 ml), followed by adding NiCl2(dppp) (2.5 g) as a catalyst, agitating the mixture at −10° C. for 15 minutes, dropwise adding therto a Grignard reagent obtained by reacting p-bromoanisole (96.5 g) with magnesium in THF, agitating the mixture in an ice bath for one hour, removing the ice bath, agitating it at room temperature for 3 hours, allowing it to stand overnight, adding toluene (500 ml), further adding 6N-hydrochloric acid, separating the resulting organic layer, washing it with water, then with an alkali and further with water till the washing water became neutral, drying with MgSO4, distilling off toluene, purifying the residue according to column chromatography using activated alumina (300 g) and toluene as an eluent, concentrating, and recrystallizing from ethyl acetate (700 ml) to obtain 3-(4'-methoxyphenyl)-6-(4'-propylphenyl)-pyridazine (70 g). This product had a m.p. of 155.9° C., exhibited nematic phase and formed an isotropic liquid at 254° C.

(b) Preparation of
3-(4'-hydroxyphenyl)-6-(4'-propylphenyl)-pyridazine

A mixed solution of 3-(4'-methoxyphenyl)-6-(4'-propylphenyl)-pyridazine (70 g) obtained in the above item a), hydrobromic acid (48%) (350 ml) and acetic acid (1 l) was heated under reflux for 40 hours, followed by adding water (1 l), filtering off deposited crystals dissolving the crystals in ethanol (2 l), adding 2N-NaOH to make the solution alkaline, further adding acetic acid, filtering off the resulting crystals and recrystallizing from a mixed solution of ethanol with chloroform (1:1) (700 ml) to obtain 3-(4'-hydroxyphenyl)-6-(4'-propylphenyl)-pyridazine (52 g). This product had a m.p. of 220°-223° C.

(c) Preparation of the captioned compound

S-5-methylheptanoic acid (0.8 g) was added to a mixture of 3-(4'-hydroxyphenyl)-6-(4'-propylphenyl)-pyridazine (1.0 g) obtained in the above item b), N,N-dicyclohexylcarbodiimide (hereinafter abbreviated to DCCC) (1.0 g), 4-N,N-dimethylaminopyridine (hereinafter abbreviated to DMAP) (0.1 g) and methylene chloride (50 ml), followed by agitating the mixture at room temperature for 3 hours, filtering off the resulting insolubles, washing the mother liquor with water, then with an alkali and further with water to make it neutral, concentrating the resulting liquid, purifying the residue according to column chromatography using activated alumina (20 g) and toluene as an eluent and recrystallizing from ethanol (30 ml) to obtain the captioned S-3-(4'-(5''-methylheptanoyloxy)phenyl)-6-(4'-propylphenyl)-pyridazine (0.6 g). This product exhibited the following phase transition points:

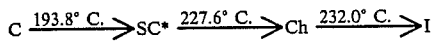

Other compounds of the formula (I) obtained in the same manner as in Examples 1 to 3 are shown in Table 1.

Example 4 (Use example 1)

The compound of Example 1 of the present invention was filled in a cell provided with transparent electrodes each obtained by applying polyvinyl alcohol as an aligning agent and rubbing the surface to subject it to a parallel aligning treatment, and having a gap between the electrodes of 2 μm, followed by providing the resulting cell between two sheets of crossed polarizers and impressing a square wave of 10V. As a result, change in the intensity of transmitted light was observed. Further, Ps according to Sowyer-Tower method, tilt angle and response time at that time were measured. The results were as follows:

| Temperature (°C.) | Ps (nC/cm²) | Tilt angle (°) | Response time (μsec) |
|---|---|---|---|
| 145 | 85 | 36.0 | 15 |
| 140 | 90 | 37.0 | 15 |
| 135 | 94 | 37.5 | 18 |
| 130 | 94 | 37.5 | 20 |
| 120 | 99 | 37.5 | 30 |

As seen from the above results, the compound of the present invention is useful as a component of liquid crystal compositions used for ferroelectric liquid crystal elements having a large Ps value, a nearly constant tilt angle irrespective of temperatures and a short response time.

Example 5 (Use example 2)

The compound of Example 2 of the present invention was added in 1% by weight to a commercially available nematic liquid crystal composition (ZLI-1132, tradename of a product made by Merck Co.) to prepare a chiral nematic liquid crystal composition. Its chiral pitch length was measured according to Cano wedge method. The temperature dependency of the chiral pitch length became negative as seen from the followings results:

| Temperature (°C.) | Pitch length (μm) |
|---|---|
| 20 | 32.3 |
| 30 | 31.3 |
| 40 | 30.3 |
| 50 | 29.6 |
| 60 | 28.7 |
| 70 | 27.9 |

Example 6 (Use example 3)

A nematic liquid crystal composition consisting of

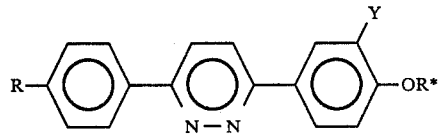

20% by weight

40% by weight

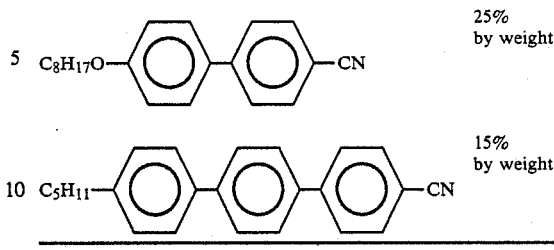

25% by weight

15% by weight was filled in a cell provided with transparent electrodes each obtained by applying polyvinyl alcohol as an aligning agent and rubbing the resulting surface to subject it to a parallel aligning treatment, and having a gap between the electrodes of 10 μm to prepare a TN type display element, which was then observed under a polarizing microscope. As a result, a reverse domain was observed to be formed. To this nematic liquid crystal composition was added the compound of No. 5 of Table 1 as a compound of the presnet invention i.e.

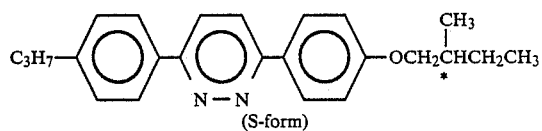

(S-form)

in a quantity of 1% by weight and a TN type cell was similarly prepared. As a result of its observation, the reverse domain was dissolved and a uniform nematic phase was observed.

What we claim is:

1. A compound expressed by the formula

R—⬡—⬡(N=N)—⬡(Y)—OR* wherein R represents a linear alkyl group of 3 to 9 carbon atoms, R* represents an optically active alkyl group of 5 to 11 carbon atoms having a methyl branch and Y represents a hydrogen atom or a fluorine atom.

2. A compound according to claim 1 wherein said R* represents an optically active 1-methylheptyl group.

3. A liquid cyrstal composition comprising at least two components at least one of which is a compound as set forth in claim 1.

* * * * *